United States Patent [19]

Iorio

[11] Patent Number: 4,812,303

[45] Date of Patent: Mar. 14, 1989

[54] HIGH DOSE CALCIUM TABLET

[75] Inventor: Theodore L. Iorio, Hingham, Mass.

[73] Assignee: Copley Pharmaceuticals, Inc., South Boston, Mass.

[21] Appl. No.: 857,855

[22] Filed: Apr. 3, 1986

[51] Int. Cl.⁴ .......................... A61L 9/04; A01N 59/06
[52] U.S. Cl. .......................................... 424/44; 424/156; 424/438
[58] Field of Search .......................... 424/44, 156, 438

[56] References Cited

U.S. PATENT DOCUMENTS

| | | | |
|---|---|---|---|
| 3,887,700 | 6/1975 | Bonoey et al. | 424/44 |
| 4,650,669 | 3/1987 | Alexander et al. | 424/44 |
| 4,670,248 | 6/1987 | Schricker | 424/438 |
| 4,678,661 | 7/1987 | Gergely et al. | 424/44 |

Primary Examiner—Ellis P. Robinson
Assistant Examiner—P. J. Ryan
Attorney, Agent, or Firm—Wolf, Greenfield & Sacks

[57] ABSTRACT

The invention provides a tablet that will substantially dissolve rapidly in cool tap water or juice to yield a clear or almost clear calcium solution. The constituents of the tablet are calcium carbonate, fumaric acid and a water soluble third reactant wherein the calcium carbonate and the fumaric acid are present in approximately molar equivalent amounts and the third reactant is present in an amount sufficient to control the effervescence, allowing the tablet to dissolve completely without breaking apart and leaving any appreciable residue. The third reactant is preferably calcium lactate.

6 Claims, 3 Drawing Sheets

HIGH DOSE CALCIUM TABLET

BACKGROUND OF THE INVENTION

This invention relates generally to a carboxylic acid-based effervescent tablet and more particularly to a tablet capable of delivering 400-1000 milligrams of calcium.

Calcium is found in nearly all organized body tissues and is the most abundant mineral in the body. It is an essential dietary element playing a role in nerve transmission, muscle function and blood coagulation and is essential for maintaining a normal heart beat. Additionally, calcium in combination with phosphorous forms the basic building block of skeletal tissue, teeth and bones.

Osteoporosis is a demineralization of bone that can be accompanied by bone deformation, severe pain and pathological fracture. Aging women are particularly susceptible to osteoporosis. It is widely believed that dietary supplements of calcium can retard the development or progression of this disease.

While calcium occurs naturally in certain food products, it is believed desirable to provide an increased dosage of calcium through a dietary supplement. Various calcium supplements are currently available in chewable tablets which rely on stomach acid to convert the calcium to its useful ionized form. Chewable tablets, however, are considered undesirable by many consumers due to their unpleasant chalky taste and side effects. Such tablets are commonly made from calcium carbonate. Ingesting such tablets may result in side effects including discomfort associated with the release of carbon dioxide as the calcium carbonate reacts with stomach acids and discomfort associated with the release of stomach acids as the calcium carbonate raises the pH of the stomach contents. This latter discomfort is commonly known as acid rebound. Raising the pH of the stomach contents may also inactivate the digestive enzymes.

An alternative to a chewable tablet is a tablet that would dissolve in a liquid to produce a solution of calcium containing the desired dosage. This solution could be ingested by drinking instead of chewing. It is known that calcium carbonate can be reacted with ascorbic acid to produce a calcium salt that is soluble in water. Ascorbic acid, however, is an undesirable reactant because it is expensive and because tablets made from calcium carbonate and ascorbic acid may deliver excessive doses of vitamin C.

It is an object of the invention to provide a tablet that will dissolve in cool tap water or juice in under two and one half minutes to produce a solution having a dose of calcium of at least 400 milligrams.

Another object of the invention is to provide a tablet that will dissolve completely in cool tap water or juice to produce a clear or almost clear solution having a dose of calcium of at least 400 milligrams.

Another object of the invention is to provide a water-soluble tablet providing a dose of calcium of at least 400 milligrams which is less expensive to produce than other known water-soluble calcium-delivering tablets.

It is still another object of the invention to provide a calcium-delivering effervescent tablet that will not rise to the surface of water until at least one-half of the tablet has dissolved.

SUMMARY OF THE INVENTION

The invention provides a tablet that will substantially dissolve rapidly in cool tap water or juice to yield a clear or almost clear calcium solution. The tablet may dissolve in less than two and one half minutes and may deliver a dose of at least 400 mg of calcium. The tablet may not rise to the surface of the dissolving liquid until at least one-half of the tablet has dissolved. The constituents of the tablet are calcium carbonate, fumaric acid and a water soluble third reactant wherein the calcium carbonate and the fumaric acid are present in approximately molar equivalent amounts and the third reactant is present in an amount sufficient to control the effervescence, allowing the tablet to dissolve completely without breaking apart and leaving any appreciable residue. The third reactant is preferably calcium lactate.

DETAILED DESCRIPTION OF THE PREFERRED EMBODIMENTS

It is known that calcium carbonate reacts with fumaric acid in the presence of water to form calcium fumarate, carbon dioxide and water.

$$CaCO_3 + C_4H_4O_4 \rightarrow CaC_4H_2O_4 + CO_2 + H_2O$$

Calcium fumarate in solution provides a biologically ready source of calcium ions to the body if ingested. Fumeric acid is enormously less expensive than ascorbic acid and is therefore a highly desirable reactant.

A tablet having powdered calcium carbonate and powdered fumaric acid in approximately molar equivalents will ordinarily, when added to water, effervesce rapidly and break apart leaving particles undissolved. This incomplete reaction takes about three minutes for a tablet capable of delivering a dose of calcium at about 600 mg. The tablet will also rise to the surface of the water immediately. This dramatically reduces the vigorous mixing that occurs when an effervescent tablet dissolves below the surface of the solvent allowing the bubbles generated to rise through the solution.

Figure 1:
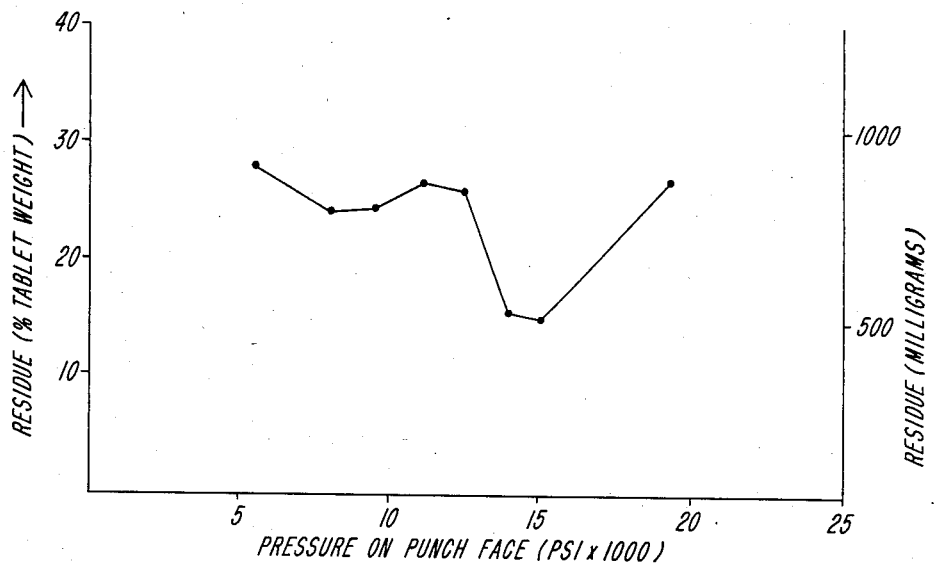
FIG. 1 graph of residue (as % or mg) versus punch face pressure.

As shown in FIG. 1, the amount of undissolved particles or residue can be reduced to approximately 15% of the total tablet weight (or about 500 mg), but not eliminated, by varying the pressure conditions under which the calcium carbonate and fumeric acid are tableted. The cloudy appearance and unpleasant taste and texture of a solution containing this amount of residue, however, are undesirable to consumers.

Applicant has discovered that the above unacceptable reaction can be controlled and caused to go to completion by adding a third reactant, such as calcium lactate, to the tablet. In addition to causing the reaction to go to completion, the calcium lactate dissolves and provides additional calcium ions to the solution as the reaction of the calcium carbonate and fumaric acid proceeds.

The clear solution has a pleasant taste and texture. Ingesting the solution does not result in the discomfort associated with ingesting chewable tablets. The release of carbon dioxide occurs as the tablet dissolves in the solvent, rather than in the stomach, and the pH of the solution is at about 5 which does not cause significant acid rebound or significant inactivation of digestive enzymes. It is preferable to use an excess of fumaric acid (approximately 1.3 moles of fumaric acid to 1.0 moles of calcium carbonate) to further guard against acid rebound and inactivation of digestive enzymes. The excess fumaric acid lowers the pH of the solution to an optimal pH of about 4.3. This also enhances the pleasant taste of the solution.

Figure 2:
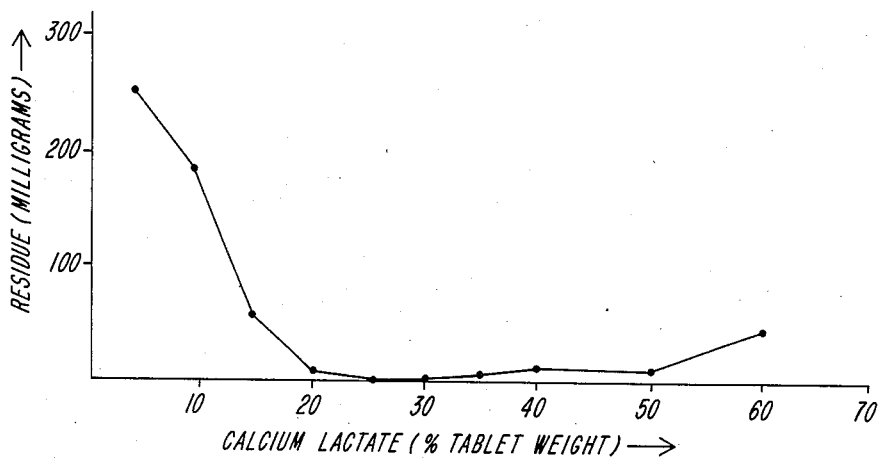
FIG. 2 graph of residue (mg) versus calcium lactate (as percentage of total tablet weight).

Tablets containing calcium carbonate and fumaric acid in approximately molar equivalent amounts and containing varying amounts of calcium lactate were prepared. FIG. 2 is a graph plotting the percent by weight of calcium in the tablet versus the amount of residue remaining after dissolving the tablets in about five ounces of water at a temperature of about 20° C. The graph plots the following data:

| % Calcium Lactate (By Weight) | Residue (Milligrams) | % Calcium Lactate (By weight) | Residue (Milligrams) |
|---|---|---|---|
| 5 | 260 | 30 | 0 |
| 10 | 180 | 35 | 10 |
| 15 | 70 | 40 | 20 |
| 20 | 10 | 50 | 10 |
| 25 | 0 | 60 | 50 |

As illustrated, tablets containing between about 20% and 50% by weight calcium lactate will dissolve almost completely (residue 1% total tablet weight), with the optimal range between about 22% and 32% calcium lactate.

Figure 3:
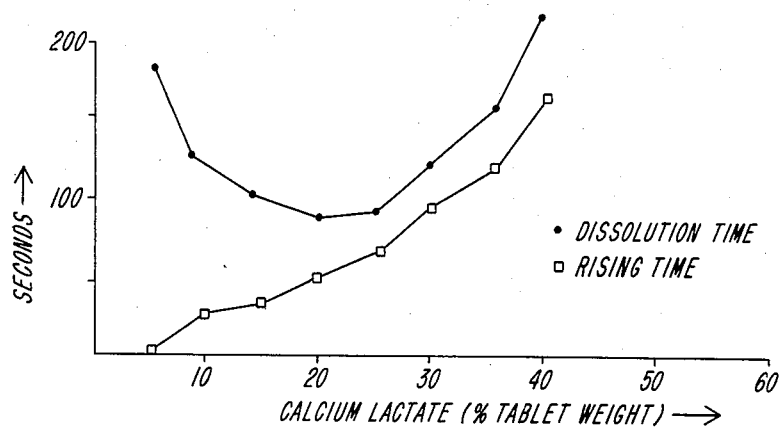
FIG. 3 graph of dissolution time and rising time (in seconds) versus calcium lactate (as percentage of total tablet weight).

Applicant has also discovered that the amount of calcium lactate in the tablet influences the time it takes for the tablet to dissolve and the time it takes for the tablet to rise to the surface. FIG. 3 is a graph of these variables as a function of percent by weight of calcium lactate; FIG. 3 plots the following data:

| % Calcium Lactate | Dissolution Time/seconds | Rising Time/seconds |
|---|---|---|
| 5 | 180 | 1 |
| 10 | 127 | 30 |
| 15 | 108 | 42 |
| 20 | 88 | 53 |
| 25 | 95 | 60 |
| 30 | 125 | 90 |
| 35 | 152 | 114 |
| 40 | 202 | 150 |
| 50 | 1200 | 265 |

As illustrated, tablets containing between about 20% to 40% calcium lactate do not rise to the surface until at least half of the total dissolution time has elapsed. At 20%, the total dissolution time was 88 seconds and the tablet did not rise to the surface until 53 seconds had elapsed. At 40% calcium lactate, the total dissolution time was 202 seconds and the tablet did not rise to the surface until 150 seconds had elapsed. Surprisingly, the amount of calcium lactate (22.8%) which caused the lowest dissolution time (about 85 seconds) fell within the range defining the amount of calcium lactate required for the tablet to dissolve completely. In fact, this amount of calcium lactate may represent the minimum amount required to allow the tablet to dissolve completely. Likewise, a tablet containing 22.8% calcium lactate does not rise to the surface until the reaction time is about 60% over, which provides suitable mixing of the solution by the carbon dioxide bubbles generated. Thus, applicant's tablet will completely dissolve in less than one and one half minutes to an almost clear solution.

Increasing the percentage of calcium lactate to about 40% calcium will result in a suitable tablet, but will take longer to dissolve. Likewise, as little as 18% calcium lactate will result in a suitable tablet although there will be a slight amount of undissolved reactants.

Figure 4:
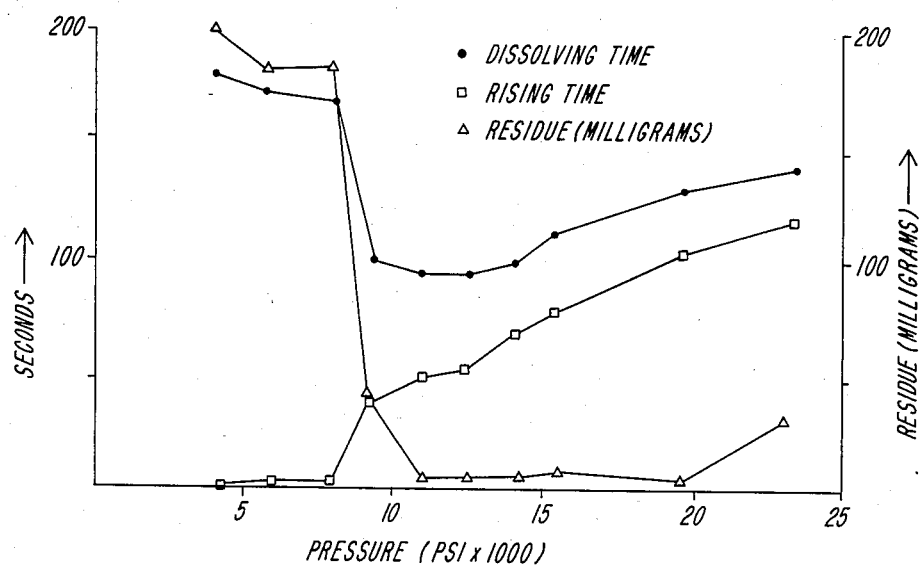
FIG. 4 graph of dissolving time and rising time (in seconds) and residue (in mgs) versus pressure.

Tablets containing 1.125 grams of calcium carbonate, 1.665 grams of fumaric acid and 0.826 grams of calcium lactate (22.8% by weight) were tabletted under various pressures in conventional tableting apparatus well known to those skilled in the art. The various tableting pressures yielded tablets having various densities and the effect of pressure and density on residue, rising time and dissolution time were measured. The data presented graphically in FIG. 4 was as follows:

| Lbs. pressure On Punch Face | Density (gm/cm$^3$) | Residue (Mg) | Dissolve Time (Secs.) | Rising Time (Secs.) |
|---|---|---|---|---|
| 4,688 | 1.147 | 200 | 175 | 2 |
| 6,250 | 1.197 | 180 | 170 | 3 |
| 7,813 | 1.229 | 180 | 164 | 3 |
| 9,375 | 1.264 | 50 | 100 | 46 |
| 10,938 | 1.303 | 10 | 95 | 57 |
| 12,500 | 1.328 | 10 | 95 | 62 |
| 14,063 | 1.341 | 10 | 100 | 73 |
| 15,625 | 1.363 | 20 | 110 | 82 |
| 19,531 | 1.415 | 10 | 120 | 97 |
| 23,438 | 1.455 | 30 | 140 | 120 |

Tablets having densities between about 1.30 and about 1.42 gm/cm$^3$ will dissolve completely. Tablets having densities above or below this range yield tablets that may not dissolve completely and often leave appreciable residues, greater than about 30 mg. As density increases, so does dissolution time. Optimally, the density is as low as possible, here between about 1.30 and 1.33 gm/cm$^3$, which represents the fastest dissolution time (95 seconds) and an acceptable rising time (about 60 seconds).

The particle size of the calcium lactate was also found to influence the amount of residue remaining, the dissolution time and the rising time. Particle size was controlled by screening the granular reactant twice. The calcium lactate was first screened through a mesh having a pore size defining the largest particle diameter for a particle size range and the material passing through the mesh was collected. Next, the collected material was screened in a mesh having a pore size defining the smallest diameter for the particle size range and the material not passing through the mesh was collected. The theoretical average was selected as the midpoint within the range and may not in fact be the actual average particle size.

For tablets containing 22.8% by weight calcium lactate and tabletted under 10,938 psi, the data was as follows:

| Range of Particle Size (Microns) | Theoretical Average (Microns) | Residue Remaining (Mg) | Dissolution Time (sec.) | Rising Time (sec.) |
|---|---|---|---|---|
| 1–44 | 22 | 30 | 140 | 84 |
| 44–208 | 126 | 50 | 102 | 39 |
| 208–420 | 314 | 90 | 115 | 34 |
| 420–590 | 505 | 90 | 120 | 39 |
| 590–840 | 715 | 180 | 130 | 2 |
| 840–2000 | 1420 | 180 | 160 | 1 |

Figure 5:
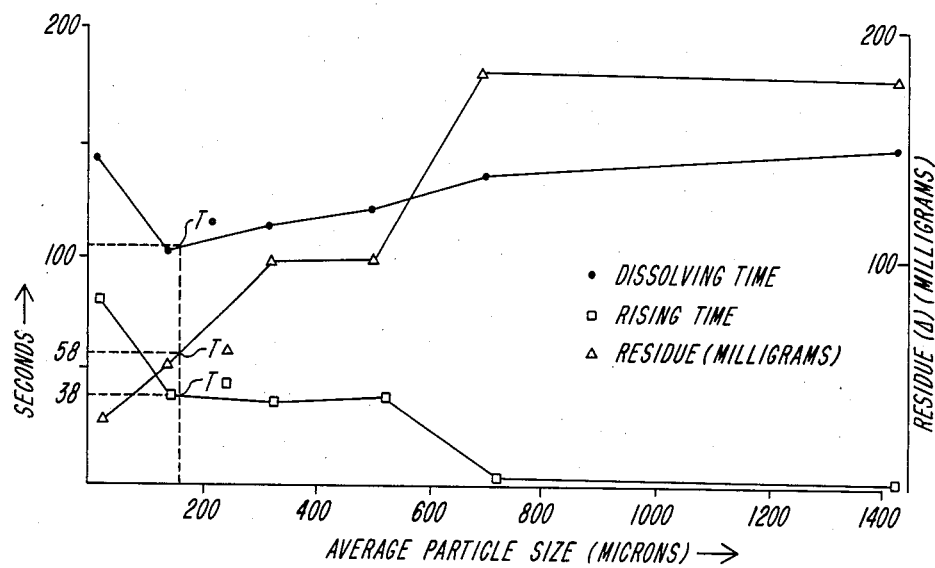
FIG. 5 graph of dissolving time and rising, time (in seconds) and residue (in mgs) versus average particle size (in microns).

As shown in FIG. 5, the least amount of residue (30 mg) occurred with a particle size range of 1–44 microns. The dissolution time for this particle size range, however, was 140 seconds, more than two minutes. Particle size range 44–208 microns had a more desirable dissolution time (102 seconds), but left a less desirable amount of residue (50 mg) and had a less desirable rising time (39 seconds). The same was true for ranges above 44–208 microns. Surprisingly, a particle size range of 20–250, with a theoretical average of 145 microns, left virtually no residue, dissolved in 95 seconds and rose to the surface only after 5/ seconds. These features were quite unexpected since the values based on the theoretical average particle size (indicated by the letter T in FIG. 5) were 58 mg for residue, 104 seconds for dissolution time and 38 seconds for rising time.

While applicant does not wish to be bound by any theory, applicant believes that the addition of the calcium lactate serves to slow the rate at which water is contacted with the reactants and, accordingly, the evolution of carbon dioxide gas. Controlling the effervescence prevents the tablet from being broken apart and keeps the reactants in intimate contact at high concentrations for a longer time allowing the reaction to go to completion. Slowing the effervescence may also allow the tablet to stay submerged for a longer period of time. It is also believed that the action of the rising bubbles makes the solution more acidic which also promotes the dissolution of any suspended calcium. Other water soluble reactants may be substituted for calcium lactate to serve the same function that the calcium lactate serves, that is, to control the effervescent reaction and keep the reactants in intimate contact for a longer time, allowing the tablet to dissolve completely.

The tableting pressure, amounts of reactants, and particle size appear to be interdependent and varying one of these factors may result in a need to alter another to provide a tablet having optimal properties.

Other substances such as vitamins, minerals and tableting aids may be included in the tablets as desired. Such substances, however, must not significantly interfere with the reaction of the calcium carbonate and fumaric acid, or be present in amounts that prevent the tablet from dissolving completely, cause the tablet to rise to the surface too quickly, or cause the tablet to dissolve too slowly. Examples of useful vitamins are ascorbic acid, thiamine mononitrate and pyridixine hydrochlorate. Examples of useful minerals are sodium bicarbonate, potassium bicarbonate, magnesium chloride and calcium ascorbate. Coloring, flavoring, sweetening or granulating agents may also be added subject to the same limitations.

The solvent may be water, juice such as orange juice, grapefruit juice, apple juice, or grape juice, or even hot beverages such as tea. Optimally, the tablet is capable of delivering between 400 and 1,000 mgs of calcium ion and dissolving in water at a temperature of about 20° C. in under two and one half minutes. Reducing the temperature of the solvent will increase the dissolution time. Likewise, increasing the temperature of the solvent will decrease the dissolution time. For example, if tea at about 70° C. is the solvent, the dissolution time is about 20 seconds for a tablet weighing about 3.5 grams and containing 22.8% by weight calcium lactate.

EXAMPLE 1

Tablet containing 22.8% by weight calcium lactate. 1.125 grams of calcium carbonate, U.S.P. XXI, obtained from Pfizer, Inc. of New York, N. Y. was mixed with 1.665 grams of fumaric acid NF XVI obtained from Pfizer, Inc. of New York, N. Y. To this was mixed 0.826 grams of calcium lactate, U.S.P. XXI, dried form, from Sheffield Products, Norwich, N. Y. (The source of each reactant remains the same for Examples 2, 3, and 4). Prior to mixing, the particle size of the calcium lactate was controlled by screening the calcium lactate twice. First the calcium lactate was screened through a 60 mesh screen, U.S. Standard Sieve, and the material passing through the mesh was collected. Next the collected material was screened with a 625 mesh screen, U.S. Standard Sieve. The material not passing through the mesh was collected. The mixture was formed into a tablet in a conventional tableting press under a dwell pressure of 10,938 psi for about 0.1 second.

The tablet was placed in a beaker containing five ounces of tap water at about 20° C. The tablet dissolved in 85 seconds to form an almost clear solution containing about 600 mg. of calcium.

EXAMPLE 2

Tablet containing 20% by weight calcium lactate. 1.1/4 grams of calcium carbonate was mixed with 1./38 grams of fumaric acid. To this was mixed 0.24 grams of calcium lactate. Prior to mixing, the particle size of the calcium lactate was controlled by screening it as in Example 1, first through a 60 mesh screen, U.S. Standard Sieve, and next with a 625 mesh screen, U.S. Standard Sieve. The mixture was formed into a tablet in a conventional tableting press under a dwell pressure of 10,938 psi for about 0.1 second.

The tablet was placed in a beaker containing 5 ounces tap water at about 20° C. The tablet dissolved in 88 seconds to form an almost clear solution containing about 600 milligrams of calcium.

EXAMPLE 3

Tablet containing 25% by weight calcium lactate. 1.093 grams of calcium carbonate was mixed with 1.618 grams of fumaric acid. To this was mixed 0.906 grams of calcium lactate. Prior to mixing, the particle size of the calcium lactate was controlled by screening it, as in Example 1, first through a 60 mesh screen, U.S. Standard Sieve, and next with a 625 mesh screen, U.S. Standard Sieve. The mixture was formed into a tablet in a conventional tableting press under a dwell pressure of 10,938 psi for about 0.1 second.

The tablet was placed in a beaker containing 5 ounces of tap water at about 20° C. The tablet dissolved in 95 seconds to form an almost clear solution containing about 600 milligrams of calcium.

EXAMPLE 4

Tablet containing 30% by weight calcium lactate. 1.012 grams of calcium carbonate was mixed with 1.49 grams of fumaric acid. To this was mixed 1.08/ grams of calcium lactate. Prior to mixing, the particle size of the calcium lactate was controlled by screening it, as in Example 1, first through a 60 mesh screen, U.S. Standard Sieve, and next with a 625 mesh screen, U.S. Standard Sieve. The mixture was formed into a tablet in a conventional tableting press under a dwell pressure of 10,938 psi for about 0.1 second.

The tablet was placed in a beaker containing 5 ounces of tap water at about 20° C. The tablet dissolved in 125 seconds to form an almost clear solution containing about 600 milligrams of calcium.

It should be understood that various changes and modifications of the preferred embodiments may be made within the scope of this invention. Thus, it is intended that all matter contained in the above description shall be interpreted in an illustrative and not limiting sense.

What I claim is:

1. An effervescent tablet that will dissolve rapidly in cool tap water or juice to yield a clear or almost clear solution consisting essentially of,
    calcium carbonate,
    fumaric acid, and
    calcium lactate wherein said calcium carbonate and said fumaric acid are present in approximately molar equivalent amounts and said calcium lactate is present in an amount sufficient to control the effervescence, allowing the tablet to dissolve completely without breaking apart and leaving any appreciable residue.

2. A tablet as claimed in claim 1 wherein the calcium carbonate and fumaric acid are present in approximately molar equivalent amounts, and said calcium lactate is present in an amount between about 18% and 40% of the total tablet weight.

3. A tablet as claimed in claim 2 wherein the calcium lactate has a particle size of between about 20 and 250 microns.

4. A tablet as claimed in claim 1 wherein said calcium carbonate and said fumaric acid are present in approximately molar equivalent amounts and said calcium lactate is present in an amount between about 20 and 25% of the total tablet weight.

5. A tablet as claimed in claim 3 wherein said tablet has a density of between 1.3 and 1.42 $gm/cm^3$.

6. A tablet as claimed in claim 3 wherein said tablet has a density of between 1.30 and 1.33 $gm/cm^3$.

* * * * *